US012751996B2

(12) United States Patent
Xu et al.

(10) Patent No.: US 12,751,996 B2
(45) Date of Patent: Oct. 6, 2026

(54) APPLICATION OF TFF2 PROTEIN AND IFN-κ PROTEIN COMBINATION IN TREATMENT OF A NOVEL CORONAVIRUS INFECTION

(71) Applicant: Shandong Ruiying Pioneer Pharmaceutical Co., Ltd, Heze (CN)

(72) Inventors: Jianqing Xu, Shanghai (CN); Xiaoyan Zhang, Shanghai (CN); Weihui Fu, Shanghai (CN); Songhua Yuan, Shanghai (CN); Yongquan He, Shanghai (CN)

(73) Assignee: SHANDONG RUIYING PIONEER PHARMACEUTICAL CO., LTD, Heze (CN)

( * ) Notice: Subject to any disclaimer, the term of this patent is extended or adjusted under 35 U.S.C. 154(b) by 935 days.

(21) Appl. No.: 17/995,286

(22) PCT Filed: Mar. 30, 2020

(86) PCT No.: PCT/CN2020/082195

§ 371 (c)(1),
(2) Date: Sep. 30, 2022

(87) PCT Pub. No.: WO2021/195883

PCT Pub. Date: Oct. 7, 2021

(65) Prior Publication Data

US 2023/0173028 A1 Jun. 8, 2023

(51) Int. Cl.
*A61K 38/21* (2006.01)
*A61K 38/17* (2006.01)
*A61P 31/14* (2006.01)

(52) U.S. Cl.
CPC .......... *A61K 38/21* (2013.01); *A61K 38/1732* (2013.01); *A61P 31/14* (2018.01)

(58) Field of Classification Search
CPC ............................ A61K 38/21; A61K 38/1732
See application file for complete search history.

(56) References Cited

U.S. PATENT DOCUMENTS

2013/0274171 A1 10/2013 Fiala et al.

FOREIGN PATENT DOCUMENTS

| | | | | | |
|---|---|---|---|---|---|
| CN | 1617739 | A | | 5/2005 | |
| CN | 1927389 | A | * | 3/2007 | |
| CN | 103096917 | A | | 5/2013 | |
| CN | 105582526 | A | * | 5/2016 | ............. A61K 38/18 |
| CN | 107375908 | A | | 11/2017 | |
| WO | 03082196 | A2 | | 10/2003 | |
| WO | WO-2021038296 | A2 | * | 3/2021 | ............. C07K 14/59 |

OTHER PUBLICATIONS

Punta et al. The Rough Guide to In Silico Function Prediction, or How to Use Sequence and Structure Information to Predict Protein Function. PLoS Comput Biol 4(10): e1000160, 2008 (Year: 2008).*
Whisstock et al. Prediction of proteinfunction fromprotein sequence and structure. Quarterly Reviews in Biophysics. 36(3):307-340, 2007 (Year: 2007).*
Burgess et al. Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue. J. Cell Biol. 111:2129-2138, 1990 (Year: 1990).*
Song et al. A Single Amino Acid Change (Asp 533Ala53) Converts Survivin from Anti-apoptotic to Pro-apoptotic. Molecular Biology of the Cell, 15:1287-1296, Mar. 2004 (Year: 2004).*
Defeo-Jones et al. Substitution of Lysine for Arginine at Position 42 of Human Transforming Growth Factor-a Eliminates Biological Activity without Changing Internal Disulfide Bonds. Molecular and Cellular Biology, Sep. 1989, p. 4083-4086 (Year: 1989).*
Bork. Powers and Pitfalls in Sequence Analysis: The 70% Hurdle. Genome Research, 2000; 10:398-400 (Year: 2000).*
BCYY Peking Medicine Physician, The "Star Drug" to Fight Pneumonia: Interferon (IFN), Mar. 6, 2020, 5 pages [No English Language Translation Available].
Liu et al., Research and Development on Therapeutic Agents and Vaccines for COVID-19 and Related Human Coronavirus Diseases, ACS Central Science, 2020, 6:315-331.
Toshihiko, Novel Coronavirus Infection (Including SARS), Major and Secondary Research, 2013, 90(12):1679-1684 [No English Language Translation Available].
European Patent Office, Extended European Search Report, Application No. 20928833.1, Aug. 1, 2023, 8 pages.
Japanese Patent Office, Notice of Reasons for Refusal, Application No. 2022-559919, Aug. 29, 2023, 10 pages.
The State Intellectual Property Office of People's Republic of China, First Office Action and Search Report, Application No. 202010239633.3, May 5, 2023, 12 pages.
Chen et al., Rational Administration and Pharmaceutical Care of Interferon Alpha Nebulization Therapy in COVID-19, Chinese Journal of Hospital Pharmacy, 2020, 40(6):632-635.
Kleinschmidt-Demasters et al., Progressive Multifocal Leukoencephalopathy Complicating Treatment with Natalizumab and Interferon Beta-1a for Multiple Sclerosis, The New England Journal of Medicine, 2005, 353(4):369-374.

(Continued)

*Primary Examiner* — Vanessa L. Ford
*Assistant Examiner* — Sandra Carter
(74) *Attorney, Agent, or Firm* — Quarles & Brady LLP

(57) ABSTRACT

A TFF2 protein and an IFN-κ protein are combined to treat a novel coronavirus infection. A product comprises: (a) an IFN-κ protein; (b) a TFF2 protein; and (c) an optional pharmaceutically acceptable carrier. Provided are an application of a combination of IFN-κ protein and TFF2 protein in the preparation of a product for the treatment of a novel coronavirus infection and related diseases, and a method for using the product to treat a novel coronavirus infection and related diseases. The foregoing combination, application, and method have excellent therapeutic effects on novel coronavirus infections, and have application prospects and social benefits.

8 Claims, 3 Drawing Sheets

Specification includes a Sequence Listing.

(56) References Cited

OTHER PUBLICATIONS

Anger-Gould et al., Progressive Multifocal Leukoencephalopathy in a Patient Treated with Natalizumab, The New England Journal of Medicine, 2005, 353(4):375-381.
Nardelli et al., Regulatory Effect of IFN-k, A Novel Type 1 IFN, On Cytokine Production by Cells of the Innate Immune System, The Journal of Immunology, 2002, 169(9):4822-4830.
General Office of the National Health Commission, Novel Coronavirus Pneumonia Diagnosis and Treatment Plan, Provisional 6th Edition, 2020, 16 pages.
Rudick et al., Natalizumab plus Interferon Beta-1a for Relapsing Multiple Sclerosis, The New England Journal of Medicine, 2006, 354(9):911-923.
United Nations, Global Humanitarian Response Plan: COVID-19, 2020, 80 pages.
Wu, TFF2 Regulates LPS-Induced Macrophages Polarization and Inhibits Inflammation, Medicine and Health Sciences, 2019, 7 pages.
PCT International Search Report and Written Opinion, PCT/CN2020/082195, Dec. 31, 2020, 17 pages.

* cited by examiner

SEQUENCE LISTING

```
<160> NUMBER OF SEQ ID NOS: 16

<210> SEQ ID NO 1
<211> LENGTH: 107
<212> TYPE: PRT
<213> ORGANISM: Artificial
<220> FEATURE:
<223> OTHER INFORMATION: recombinant human hTFF2 protein

<400> SEQUENCE: 1

Met Glu Lys Pro Ser Pro Cys Gln Cys Ser Arg Leu Ser Pro His Asn
1               5                   10                  15

Arg Thr Asn Cys Gly Phe Pro Gly Ile Thr Ser Asp Gln Cys Phe Asp
            20                  25                  30

Asn Gly Cys Cys Phe Asp Ser Ser Val Thr Gly Val Pro Trp Cys Phe
        35                  40                  45

His Pro Leu Pro Lys Gln Glu Ser Asp Gln Cys Val Met Glu Val Ser
    50                  55                  60

Asp Arg Arg Asn Cys Gly Tyr Pro Gly Ile Ser Pro Glu Glu Cys Ala
65                  70                  75                  80

Ser Arg Lys Cys Cys Phe Ser Asn Phe Ile Phe Glu Val Pro Trp Cys
                85                  90                  95

Phe Phe Pro Lys Ser Val Glu Asp Cys His Tyr
            100                 105
```

<210> SEQ ID NO 2
<211> LENGTH: 107
<212> TYPE: PRT
<213> ORGANISM: Artificial
<220> FEATURE:
<223> OTHER INFORMATION: recombinant mouse mTFF2 protein

<400> SEQUENCE: 2

Met Glu Lys Pro Ser Pro Cys Arg Cys Ser Arg Leu Thr Pro His Asn
1 5 10 15

Arg Lys Asn Cys Gly Phe Pro Gly Ile Thr Ser Glu Gln Cys Phe Asp
20 25 30

Leu Gly Cys Cys Phe Asp Ser Ser Val Ala Gly Val Pro Trp Cys Phe
35 40 45

His Pro Leu Pro Asn Gln Glu Ser Glu Gln Cys Val Met Glu Val Ser
50 55 60

Ala Arg Lys Asn Cys Gly Tyr Pro Gly Ile Ser Pro Glu Asp Cys Ala
65 70 75 80

Ser Arg Asn Cys Cys Phe Ser Asn Leu Ile Phe Glu Val Pro Trp Cys
85 90 95

Phe Phe Pro Gln Ser Val Glu Asp Cys His Tyr
100 105

<210> SEQ ID NO 3
<211> LENGTH: 603
<212> TYPE: DNA
<213> ORGANISM: Homo sapiens

<400> SEQUENCE: 3
attctgcaag ccaccctggg gtgcagctga gctagacatg ggacggcgag acgcccagct 60
cctggcagcg ctcctcgtcc tggggctatg tgccctggcg ggagtgagaa aaccctcccc 120
ctgccagtgc tccaggctga gcccccataa caggacgaac tgcggcttcc ctggaatcac 180
cagtgaccag tgttttgaca atggatgctg tttcgactcc agtgtcactg gggtcccctg 240
gtgtttccac cccctcccaa agcaagagtc ggatcagtgc gtcatggagg tctcagaccg 300
aagaaactgt ggctacccgg gcatcagccc cgaggaatgc gcctctcgga agtgctgctt 360
ctccaacttc atctttgaag tgccctggtg cttcttcccg aagtctgtgg aagactgcca 420
ttactaagag aggctggttc cagaggatgc atctggctca ccgggtgttc cgaaaccaaa 480
gaagaaactt cgccttatca gcttcatact tcatgaaatc ctgggttttc ttaaccatct 540
tttcctcatt ttcaatggtt taacatataa tttctttaaa taaaaccctt aaaatctgct 600
aaa 603

<210> SEQ ID NO 4
<211> LENGTH: 390
<212> TYPE: DNA
<213> ORGANISM: Homo sapiens

<400> SEQUENCE: 4
atgggacggc gagacgccca gctcctggca gcgctcctcg tcctggggct atgtgccctg 60
gcggggagtg agaaaccctc cccctgccag tgctccaggc tgagccccca taacaggacg 120
aactgcggct tccctggaat caccagtgac cagtgttttg acaatggatg ctgtttcgac 180
tccagtgtca ctggggtccc ctggtgtttc caccccctcc caaagcaaga gtcggatcag 240
tgcgtcatgg aggtctcaga ccgaagaaac tgtggctacc cgggcatcag ccccgaggaa 300
tgcgcctctc ggaagtgctg cttctccaac ttcatctttg aagtgccctg gtgcttcttc 360

```
ccgaagtctg tggaagactg ccattactaa                                   390


<210> SEQ ID NO 5
<211> LENGTH: 571
<212> TYPE: DNA
<213> ORGANISM: Mus musculus

<400> SEQUENCE: 5

attctgcagg ctgcccaggt ccagtggagc agacatgcga cctcgaggtg cccccctgct    60

ggcagtggtc ctggttttgg gactgcatgc tctggtagag ggcgagaaac cttccccctg   120

tcggtgctcc aggctgacac cccacaacag aaagaactgt ggcttcccgg gcatcaccag   180

tgagcagtgc tttgatcttg gatgctgctt tgactctagc gtcgctgggg tcccttggtg   240

tttccaccca cttccaaacc aagaatcgga gcagtgtgtc atggaagtgt cagctcgcaa   300

gaattgtggg tacccgggca tcagtcccga ggactgtgcc agtcgaaact gctgcttttc   360

caacctgatc tttgaagtgc cctggtgttt cttcccacag tctgtggaag attgtcacta   420

ctgagagttg ctactgccga gccacccgtt ccctgggagc tgcaagccag aagaaagttt   480

caaccagact tcatcaatct ctggggtttc taaaaccatc ttgaccctta gcagtggcta   540

gacacagcat tttccaagta aagaaaagtt g                                 571


<210> SEQ ID NO 6
<211> LENGTH: 390
<212> TYPE: DNA
<213> ORGANISM: Mus musculus

<400> SEQUENCE: 6

atgcgacctc gaggtgcccc cctgctggca gtggtcctgg ttttgggact gcatgctctg    60

gtagagggcg agaaaccttc cccctgtcgg tgctccaggc tgacacccca caacagaaag   120

aactgtggct tcccgggcat caccagtgag cagtgctttg atcttggatg ctgctttgac   180

tctagcgtcg ctggggtccc ttggtgtttc cacccacttc caaaccaaga atcggagcag   240

tgtgtcatgg aagtgtcagc tcgcaagaat tgtgggtacc cgggcatcag tcccgaggac   300

tgtgccagtc gaaactgctg cttttccaac ctgatctttg aagtgccctg gtgtttcttc   360

ccacagtctg tggaagattg tcactactga                                   390


<210> SEQ ID NO 7
<211> LENGTH: 181
<212> TYPE: PRT
<213> ORGANISM: Artificial
<220> FEATURE:
<223> OTHER INFORMATION: recombinant human hIFN-k protein

<400> SEQUENCE: 7

Met Leu Asp Cys Asn Leu Leu Asn Val His Leu Arg Arg Val Thr Trp
1               5                   10                  15

Gln Asn Leu Arg His Leu Ser Ser Met Ser Asn Ser Phe Pro Val Glu
            20                  25                  30

Cys Leu Arg Glu Asn Ile Ala Phe Glu Leu Pro Gln Glu Phe Leu Gln
        35                  40                  45

Tyr Thr Gln Pro Met Lys Arg Asp Ile Lys Lys Ala Phe Tyr Glu Met
    50                  55                  60

Ser Leu Gln Ala Phe Asn Ile Phe Ser Gln His Thr Phe Lys Tyr Trp
65                  70                  75                  80

Lys Glu Arg His Leu Lys Gln Ile Gln Ile Gly Leu Asp Gln Gln Ala
```

```
                85                  90                  95

Glu Tyr Leu Asn Gln Cys Leu Glu Glu Asp Lys Asn Glu Asn Glu Asp
            100                 105                 110

Met Lys Glu Met Lys Glu Asn Glu Met Lys Pro Ser Glu Ala Arg Val
        115                 120                 125

Pro Gln Leu Ser Ser Leu Glu Leu Arg Arg Tyr Phe His Arg Ile Asp
    130                 135                 140

Asn Phe Leu Lys Glu Lys Lys Tyr Ser Asp Cys Ala Trp Glu Ile Val
145                 150                 155                 160

Arg Val Glu Ile Arg Arg Cys Leu Tyr Tyr Phe Tyr Lys Phe Thr Ala
                165                 170                 175

Leu Phe Arg Arg Lys
            180
```

<210> SEQ ID NO 8
<211> LENGTH: 179
<212> TYPE: PRT
<213> ORGANISM: Artificial
<220> FEATURE:
<223> OTHER INFORMATION: recombinant mouse mIFN-k protein

<400> SEQUENCE: 8

```
Met Leu Asn Cys Val Tyr Leu Asp Asp Ser Ile Leu Glu Asn Val Lys
1               5                   10                  15

Leu Leu Gly Ser Thr Met Thr Gly Phe Pro Leu Arg Cys Leu Lys Asp
            20                  25                  30

Ile Thr Asp Phe Lys Phe Pro Lys Glu Ile Leu Pro Tyr Ile Gln His
        35                  40                  45

Met Lys Arg Glu Ile Asn Ala Val Ser Tyr Arg Ile Ser Ser Leu Ala
    50                  55                  60

Leu Thr Ile Phe Asn Leu Lys Gly Ser Ile Pro Pro Val Thr Glu Glu
65                  70                  75                  80

His Trp Glu Arg Ile Arg Ser Gly Leu Phe Lys Gln Val Arg Gln Ala
                85                  90                  95

Gln Glu Cys Phe Met Asp Glu Glu Lys Glu Asn Arg Glu His Pro His
            100                 105                 110

Ser Glu Asp Phe Leu Thr Val Tyr Leu Glu Leu Gly Lys Tyr Phe Phe
        115                 120                 125

Arg Ile Lys Lys Phe Leu Ile Asn Lys Lys Tyr Ser Phe Cys Ala Trp
    130                 135                 140

Lys Ile Val Thr Val Glu Ile Arg Arg Cys Phe Ile Ile Phe Ser Lys
145                 150                 155                 160

Ser Arg Lys Leu Leu Lys Met Ile Ser Glu Ser Pro Thr Phe Lys Gln
                165                 170                 175

Glu Leu Lys
```

<210> SEQ ID NO 9
<211> LENGTH: 1140
<212> TYPE: DNA
<213> ORGANISM: Homo sapiens

<400> SEQUENCE: 9

```
ggatttttta gcttgcaaaa aaaatgagca ccaaacctga tatgattcaa aagtgtttgt      60

ggcttgagat ccttatgggt atattcattg ctggcaccct atccctggac tgtaacttac     120

tgaacgttca cctgagaaga gtcacctggc aaaatctgag acatctgagt agtatgagca     180
```

-continued attcatttcc tgtagaatgt ctacgagaaa acatagcttt tgagttgccc caagagtttc 240
tgcaatacac ccaacctatg aagagggaca tcaagaaggc cttctatgaa atgtccctac 300
aggccttcaa catcttcagc caacacacct tcaaatattg gaaagagaga cacctcaaac 360
aaatccaaat aggacttgat cagcaagcag agtacctgaa ccaatgcttg gaggaagaca 420
agaatgaaaa tgaagacatg aaagaaatga aagagaatga gatgaaaccc tcagaagcca 480
gggtccccca gctgagcagc ctggaactga ggagatattt ccacaggata gacaatttcc 540
tgaaagaaaa gaaatacagt gactgtgcct gggagattgt ccgagtggaa atcagaagat 600
gtttgtatta cttttacaaa tttacagctc tattcaggag gaaataagaa tcatctacct 660
tcaagcaaga attaacagag attgtggcta cgcaaatgca ccaaaaaagg gtgaaatata 720
tctgaaatgt acctggttct gcccttggaa gccatttcct gctcatgcca ctaacagcat 780
gctgccaaac tgttcagatt caagattatt ccaagcgcag ggcccaaatg ttatagccaa 840
agaaagtctt atgataaaag tgaggcaaat ttcagccaag aagttagaag agatgtttaa 900
aagaacaaga acaaattgtg gatcatggta tatgcaggct atcagcagaa ggatcagaca 960
ataaaatgag ttagtgcaaa ccatttagta aaaataacta tcagcagagt tgttccagat 1020
taaaaatagt actacaagct tgtaaaggag ttaggacatg caagctactg agcataaaat 1080
atatacttgc tatttttcat gactttctct aataaagtct ttgcctgttc tctctaataa 1140

<210> SEQ ID NO 10
<211> LENGTH: 624
<212> TYPE: DNA
<213> ORGANISM: Homo sapiens

<400> SEQUENCE: 10
atgagcacca aacctgatat gattcaaaag tgtttgtggc ttgagatcct tatgggtata 60
ttcattgctg gcaccctatc cctggactgt aacttactga acgttcacct gagaagagtc 120
acctggcaaa atctgagaca tctgagtagt atgagcaatt catttcctgt agaatgtcta 180
cgagaaaaca tagcttttga gttgccccaa gagtttctgc aatacaccca acctatgaag 240
agggacatca agaaggcctt ctatgaaatg tccctacagg ccttcaacat cttcagccaa 300
cacaccttca aatattggaa agagagacac ctcaaacaaa tccaaatagg acttgatcag 360
caagcagagt acctgaacca atgcttggag gaagacaaga atgaaaatga agacatgaaa 420
gaaatgaaag agaatgagat gaaaccctca gaagccaggg tcccccagct gagcagcctg 480
gaactgagga gatatttcca caggatagac aatttcctga aagaaaagaa atacagtgac 540
tgtgcctggg agattgtccg agtggaaatc agaagatgtt tgtattactt ttacaaattt 600
acagctctat tcaggaggaa ataa 624

<210> SEQ ID NO 11
<211> LENGTH: 872
<212> TYPE: DNA
<213> ORGANISM: Mus musculus

<400> SEQUENCE: 11
ctaagcacca gggttgagaa tgactccaaa gtttttatgg ctggtggccc ttgtggctct 60
atacattccg cccatccaat ctctgaactg tgtttacctg gatgatagca tcttggaaaa 120
tgtgaaactt ctgggcagta ccatgaccgg ctttccctta agatgtctaa aagatatcac 180
agattttaag tttcctaaag agattttgcc atacatccag catatgaaaa gggagataaa 240
cgccgtctcc tatcgtatat cctctctggc actaactatc ttcaatctta aaggctccat 300

```
ccctccagtg acagaggaac actgggaacg tatcagatcg ggacttttca aacaagtgcg    360

gcaagctcaa gagtgcttca tggacgagga gaaagagaac agggaacatc ctcactccga    420

ggacttcctg acagtctacc tggagttggg caagtatttc ttcagaatca aaaagttcct    480

gataaataag aaatacagtt tctgtgcatg gaagattgtc acagtggaaa taagaagatg    540

tttcattata ttttccaagt ccagaaaact actcaaaatg atatcagaat cacccacctt    600

caagcaagaa cttaaataga agctgcaatt gctcaaatgt ctccaagaac gctttattct    660

aaagccatta ccaggatgct gctaatgcta ccttcagatg caagactttt caagttcagg    720

gttcaaggca gtgcagtcaa agaaagtctt aagcaaaaga tgaacttcag tggaaaagtt    780

agcagaaatg ttaacttata ataaaaccaa agttatacat aaaaaaaaaa aaaaaaaaaa    840

aaaaaaaaaa aaaaaaaaaa aaaaaaaaaa aa                                  872
```

<210> SEQ ID NO 12
<211> LENGTH: 600
<212> TYPE: DNA
<213> ORGANISM: Mus musculus

<400> SEQUENCE: 12

```
atgactccaa agtttttatg gctggtggcc cttgtggctc tatacattcc gcccatccaa     60

tctctgaact gtgtttacct ggatgatagc atcttggaaa atgtgaaact tctgggcagt    120

accatgaccg gctttccctt aagatgtcta aaagatatca cagattttaa gtttcctaaa    180

gagattttgc catacatcca gcatatgaaa agggagataa acgccgtctc ctatcgtata    240

tcctctctgg cactaactat cttcaatctt aaaggctcca tccctccagt gacagaggaa    300

cactgggaac gtatcagatc gggacttttc aaacaagtgc ggcaagctca agagtgcttc    360

atggacgagg agaaagagaa cagggaacat cctcactccg aggacttcct gacagtctac    420

ctggagttgg gcaagtattt cttcagaatc aaaaagttcc tgataaataa gaaatacagt    480

ttctgtgcat ggaagattgt cacagtggaa ataagaagat gtttcattat attttccaag    540

tccagaaaac tactcaaaat gatatcagaa tcacccacct tcaagcaaga acttaaatag    600
```

<210> SEQ ID NO 13
<211> LENGTH: 29
<212> TYPE: DNA
<213> ORGANISM: Artificial
<220> FEATURE:
<223> OTHER INFORMATION: TFF2 forward primer

<400> SEQUENCE: 13

```
cgctctagaa tgcgacctcg aggtgcccc                                       29
```

<210> SEQ ID NO 14
<211> LENGTH: 29
<212> TYPE: DNA
<213> ORGANISM: Artificial
<220> FEATURE:
<223> OTHER INFORMATION: TFF2 reverse primer

<400> SEQUENCE: 14

```
cctggatcct cagtagtgac aatcttcca                                       29
```

<210> SEQ ID NO 15
<211> LENGTH: 25
<212> TYPE: DNA
<213> ORGANISM: Artificial
<220> FEATURE:

-continued

```
<223> OTHER INFORMATION: IFN-k forward primer

<400> SEQUENCE: 15

cgctctagaa tgagcaccaa acctg                                         25


<210> SEQ ID NO 16
<211> LENGTH: 24
<212> TYPE: DNA
<213> ORGANISM: Artificial
<220> FEATURE:
<223> OTHER INFORMATION: IFN-k reverse primer

<400> SEQUENCE: 16

tctggatcct tatttcctcc tgaa                                          24
```

APPLICATION OF TFF2 PROTEIN AND IFN-κ PROTEIN COMBINATION IN TREATMENT OF A NOVEL CORONAVIRUS INFECTION

CROSS-REFERENCE TO RELATED APPLICATION

This application represents the U.S. national stage entry of International Application No. PCT/CN2020/082195 filed Mar. 30, 2020, the disclosure of which is incorporated herein by reference in its entirety and for all purposes.

REFERENCE TO A SEQUENCE LISTING SUBMITTED VIA EFS-WEB

The content of the ASCII text file of the sequence listing named "850766_00127_ST25.txt", which is 13.5 kb in size, created on Sep. 26, 2022, and electronically submitted via EFS-Web herewith the application, is incorporated herein by reference in its entirety.

FIELD OF THE DISCLOSURE

The present disclosure relates to the medical and biotechnology field, and specifically, to the combination of TFF2 protein and IFN-κ, the use of the combination in the preparation of a product for the treatment of novel coronavirus infection and related conditions, and the method for the treatment of novel coronavirus infection and related conditions by using the product.

BACKGROUND

Novel coronavirus pneumonia (Corona Virus Disease 2019, COVID-19), referred to as "COVID-19 pneumonia", refers to the pneumonia caused by the novel coronavirus infection. The clinical manifestations of the novel coronavirus pneumonia are mainly fever, dry cough, fatigue, and a small percentage of patients are accompanied by symptoms such as nasal congestion, runny nose, sore throat, myalgia, and diarrhea. Serious patients often develop dyspnea and/or hypoxemia one week after onset, and severe cases can rapidly progress to acute respiratory distress syndrome, septic shock, difficult-to-tackle metabolic acidosis, coagulation dysfunction, and multiple organ failure etc. It is worth noting that during the course of the disease, patients displaying serious and critical symptoms have moderate to low fever or even no obvious fever.

From December 2019 to Mar. 30, 2020, a total of 82,451 cases of novel coronavirus pneumonia have been diagnosed in China, 638,946 cases overseas, and 33,953 deaths worldwide. More than 180 countries and regions around the world have reported cases of new coronary pneumonia, and the global epidemic is still developing. On Mar. 11, 2020, the novel coronavirus epidemic has been declared a global pandemic by the World Health Organization. On Mar. 25, 2020, the United Nations launched the "Global Humanitarian Response Plan for COVID-19", which aims to help the world's most vulnerable countries fight the epidemic, protect millions of lives, and prevent the virus from continuing to spread across countries.

These data fully demonstrate that the novel coronavirus infection has caused a serious global epidemic, and its social and even global harm is huge and must be paid great attention.

The 2019 novel coronavirus (2019-nCoV) that causes the novel coronavirus pneumonia belongs to the beta genus coronavirus with an envelope. It is the seventh known coronavirus that can infect humans, and the other six are HCoV-229E, HCoV-OC43, HCoV-NL63, HCoV-HKU1, SARS-CoV (which causes severe acute respiratory syndrome) and MERS-CoV (which causes Middle East respiratory syndrome).

Although the novel coronavirus belongs to the coronavirus, it has many different properties and manifestations from other coronaviruses. For example, the differences between 2019-nCoV infection and SARS virus infection may include: (a) in terms of genetic characteristics, the genetic characteristics of 2019-nCoV are significantly different from SARS-CoV (and from MERS-CoV), and have a homology of more than 85% with bat SARS-like coronaviruses; (b) in terms of clinical manifestations, SARS-CoV can cause severe acute respiratory syndrome, with main symptoms including fever, cough, headache, muscle pain and respiratory tract infection symptoms, while the novel coronavirus shows slow onset, with relatively mild symptoms and stronger concealment; (c) in terms of infectivity, the SARS virus is only highly contagious after occurrence of symptoms such as fever and pneumonia, while the novel coronavirus has an incubation period of about 10 days or even longer during which it is contagious. Therefore, further targeted exploration and research are still needed for the prevention and treatment of novel coronavirus infection.

According to the "Novel Coronavirus Pneumonia Diagnosis and Treatment Plan (Provisional $7^{th}$ Edition)", China's current medicine treatments for novel coronavirus pneumonia mainly include: antiviral therapies, such as α-interferon, lopinavir/ritonavir, ribavirin, chloroquine phosphate, arbidol and other antiviral drugs; immunotherapies, such as tocilizumab; traditional Chinese medicines (TCMs), including ready-made medicines such as Huoxiang Zhengqi capsules, Jinhua Qinggan granules, Lianhua Qingwen capsules, Qingwen Jiedu capsules and prescriptions such as Qingfei Paidu decoction. Among these medicines, chloroquine and Lianhua Qingwen capsules are especially effective (according to the report and data shared by Academician Zhong Nanshan at the China-EU Anti-epidemic Experience Exchange Meeting on March 25). In addition, according to clinical medicine research, hydroxychloroquine (also known as hydroxylchloroquine) is also the currently recommended medicine for the treatment of novel coronavirus pneumonia due to its ability of accelerating detoxification and the lower toxicity than that of chloroquine phosphate.

However, the current antiviral therapies may have certain toxic and side effects on the human body, and may lead to the emergence of resistant strains. However, TCM treatment may have different degrees of acceptance in different countries due to the unclearness of its active substances and mechanisms.

Therefore, despite the prevention and treatment methods and accumulated experience obtained in the process of fighting SARS and other viruses in the early years and during the months of fighting against the novel coronavirus pneumonia, there is still an urgent need to develop more effective medicines against the novel coronavirus infection to curb its further development and spread, thereby maintaining the health and safety of all human beings.

Unpredictability in the Effect of Combination Therapy

The use of two or more agents in combination to prevent or treat a given condition can lead to a number of potential problems. The in vivo interactions between the two agents can be complex. The efficacy of any individual agent is related to its absorption, distribution, and excretion. When two agents are introduced into the body, each affects the absorption, distribution, and excretion of the other, thereby altering the effect of the other. For example, one agent can inhibit, activate, or induce the production of enzymes involved in the metabolic pathway of the excretion of another agent. As an example, the combination of natalizumab and interferon β1-a has been reported to increase the risk of unexpected side effects (Rudick et al., New England Journal of Medicine, 354, 911-923, 2006; Kleinschmidt-DeMasters, New England Journal of Medicine, 353, 369-379, 2005; Langer-Gould, New England Journal of Medicine, 353, 369-379, 2005). Similar examples are numerous in combination therapy development.

Therefore, when two or more agents are administered to treat the same disease, it is difficult to predict whether each agent will complement or interfere with, or have no effect on the therapeutic effect of the other in the subject. The interaction between the two agents can not only affect the intended therapeutic effect of each drug, but also increase the level of toxic metabolites. This interaction also increases or decreases the side effects of each agent. When two agents are administrated to treat a disease, it is difficult to predict how the negative effects of each drug will change. Also, it is difficult to accurately predict when the effects of an interaction between two agents will manifest.

Thus, it was the state of the art at the time of filing that the effect of a combination therapy of two specific agents was unpredictable until the results of the combination study were available.

To sum up, there is an urgent need in the art to develop agents that can effectively treat novel coronavirus infection and related conditions.

SUMMARY OF THE DISCLOSURE

The present disclosure provides a product or combination that can effectively treat novel coronavirus infection and related conditions.

In one aspect of the present disclosure, provided is a product comprising:

(a) a TFF2 protein;

(b) an IFN-κ protein; and (c) optionally, a pharmaceutically acceptable carrier.

In some embodiments, the product is a pharmaceutical composition, a combination of formulations, or a kit.

In some embodiments, the TFF2 protein is selected from the group consisting of: a polypeptide comprising the sequence set forth in SEQ ID NO: 1 or 2 or a polypeptide comprising a sequence encoded by a nucleic acid molecule as set forth in any of SEQ ID NOs: 3-6, or a polypeptide that has at least 80% homology (e.g., at least 85%, 85%, 90%, 95%, 96%, 97%, 98%, 99% homology) with any of the aforementioned polypeptides and has an inflammation-modulating activity, or a polypeptide that is derived from any of the aforementioned polypeptides and has an inflammation-modulating activity; the IFN-κ protein is selected from: human IFN-κ protein or mouse IFN-κ protein, such as the protein set forth in the sequence set forth in SEQ ID NO: 7 or 8 or a polypeptide encoded by the nucleic acid molecule set forth in any of SEQ ID NOs: 9 to 12.

In some embodiments, the TFF2 protein is selected from: human TFF2 protein or mouse TFF2 protein. In some embodiments, the TFF2 protein is selected from: the polypeptide set forth in sequence SEQ ID NO: 1 or 2 or a polypeptide encoded by the nucleic acid molecule set forth in any of SEQ ID NOs: 3 to 6.

In some embodiments, the IFN-κ protein is selected from: a polypeptide comprising the sequence set forth in SEQ ID NO: 7 or 8 or a polypeptide comprising a sequence encoded by the nucleic acid molecule set forth in any of SEQ ID NOs: 9 to 12, or a polypeptide that has at least 80% homology (e.g., at least 85%, 85%, 90%, 95%, 96%, 97%, 98%, 99% homology) with any of the aforementioned polypeptides and has an antiviral activity (e.g. being capable of inhibiting virus replication, such as inhibiting the replication of novel coronavirus), or a polypeptide that is derived from any of the aforementioned polypeptides and has an antiviral activity (e.g. being capable of inhibiting virus replication, such as inhibiting the replication of novel coronavirus).

In some embodiments, the IFN-κ protein is selected from: human IFN-κ protein or mouse IFN-κ protein. In some embodiments, the IFN-κ protein is selected from: the protein set forth in sequence SEQ ID NO: 7 or 8 or a polypeptide encoded by the nucleic acid molecule set forth in any of SEQ ID NOs: 9 to 12.

In some embodiments, the amount of the TFF2 protein is from 0.1 to 100 mg, from 0.5 to 50 mg, from 1 to 40 mg, or from 5 to 30 mg.

In some embodiments, the amount of the IFN-κ protein is from 0.01 to 100 mg, from 0.05 to 80 mg, from 0.1 to 70 mg, or from 0.5 to 50 mg. Alternatively, the amount of the IFN-κ protein is from $1\times10^4$ to $1\times10^8$ active units, from $5\times10^4$ to $5\times10^7$ active units, from $1\times10^5$ to $1\times10^7$ active units, or from $5\times10^5$ to $5\times10^6$ active units.

In some embodiments, the mass ratio of TFF2 protein to IFN-κ protein is from 1:100 to 100:1, from 1:50 to 50:1, from 1:10 to 10:1, from 1:5 to 5:1, from 1:2 to 2.5:1, or from 1:1 to 2:1.

In some embodiments, the product is in a form suitable for administration of TFF2 protein and IFN-κ protein by the same or different routes selected from: aerosol inhalation, nasal instillation, spray, intravenous administration, intra-target tissue administration, or oral administration.

In some embodiments, the product is in a form suitable for simultaneous, sequential or interval administration of TFF2 protein and IFN-κ protein.

In some embodiments, the product further comprises: one or more containers containing TFF2 protein and IFN-protein, e.g., one or more containers containing unit doses of TFF2 protein and IFN-protein; means for administration; instructions for using the product, etc.

In one aspect of the present disclosure, provided is the use of TFF2 protein and IFN-κ protein in the preparation of a product of the present disclosure, wherein the product is for treating novel coronavirus infection and related conditions in a subject.

In some embodiments, the novel coronavirus infection and related conditions include: novel coronavirus pneumonia; one or more conditions associated with novel coronavirus infection selected from the group consisting of: dyspnea, hypoxemia, acute respiration distress syndrome, septic shock, metabolic acidosis, coagulopathy, multiple organ failure, pulmonary fibrosis, persistent chronic inflammation, fever, dry cough, fatigue, nasal congestion, runny nose, sore throat, myalgia and diarrhea.

In some embodiments, the subject is a human.

In another aspect of the present disclosure, provided is a method for treating novel coronavirus infection and related conditions in a subject in need thereof, comprising administering to the subject a therapeutically effective amount of a combination of TFF2 protein and IFN-κ protein. The features involved in this aspect may be as described above.

In another aspect of the present disclosure, provided is a combination of TFF2 protein and IFN-κ protein for use in the treatment of novel coronavirus infection and related conditions in a subject. The features involved in this aspect may be as described above.

Those skilled in the art can arbitrarily combine the foregoing technical solutions and technical features without departing from the disclosed concept and protection scope of the present disclosure. Other aspects of the present disclosure will be apparent to those skilled in the art in view of the disclosure herein.

DESCRIPTION OF DRAWINGS

The present disclosure will be further described below with reference to the drawings. These drawings are only intended to illustrate embodiments of the present disclosure and are not intended to limit the scope of the present disclosure.

Figure 1A:
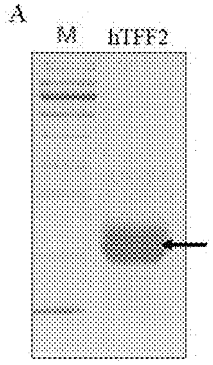
FIG. 1A: SDS-PAGE electropherogram of TFF2 protein.

In each figure, * represents $p<0.05$;  represents $p<0.01$; * represents $p<0.001$; NC represents conventional treatment control.

DETAILED DESCRIPTION OF THE DISCLOSURE

The applicant has developed TFF2 protein preparation and IFN-κ protein preparation through long-term and in-depth research, and unexpectedly found that the combination of these two agents has significant effects in the treatment of novel coronavirus infection and related conditions, the efficacy of which is even better than the currently recommended medicine hydroxychloroquine; moreover, since these two proteins are inherent proteins of the human body, and the clinical test results have also proved their low toxicity to the human body, the safety of the combined agents is relatively high. Based on related research, the present disclosure provides a combination of TFF2 protein and IFN-κ protein, its use in the preparation of a medicament for the treatment of novel coronavirus infection and related conditions, and a corresponding treatment method.

All numerical ranges provided herein are intended to expressly include all numerical values falling between the endpoints of the range and numerical ranges therebetween. Features mentioned in the present disclosure or features mentioned in the embodiments may be combined. All features disclosed in this specification may be used in combination with any form of composition, and each feature disclosed in the specification may be replaced by any alternative feature serving the same, equivalent or similar purpose. Therefore, unless otherwise stated, the disclosed features are only general examples of equivalent or similar features.

As used herein, "unit dose" and "unit dosage form" refer to a single drug administration entity.

As used herein, "about" in the context of a value or range means±10% of the recited or claimed value or range.

It should be understood that when parameter ranges are provided, the present disclosure also provides all integers and their tenths within the range. For example, "0.1-2.5 mg/day" includes 0.1 mg/day, 0.2 mg/day, 0.3 mg/day, etc. up to 2.5 mg/day. The same goes for the ratio range.

As used herein, "comprising", "having" or "including" includes "containing", "consisting mainly of", "essentially consisting of", and "comprised of"; "consisting mainly of", "essentially consisting of" and "comprised of" are specific terms of "comprising", "having", or "including".

Trefoil Factor 2 Protein (TFF2 Protein)

Trefoil factor 2 protein (TFF2 protein) was isolated from porcine pancreas by Jorgensen et al. in 1982 and is highly conserved in different species. Human trefoil factor 2 (hTFF2) and murine trefoil factor 2 (mTFF2) contain the same number of amino acids, and the amino acid sequence homology reaches 82%. The mature TFF2 protein consists of 106 amino acids, has a molecular weight of about 7-12 kD, and contains 4 exons and two symmetrical trefoil domains, so it is extremely stable in structure, and is acid-resistant, heat-resistant and resistant to protease hydrolysis. It is expressed in goblet cells in the neck of gastric mucosa.

As used herein, the terms "trefoil factor 2 protein", "TFF2 protein" and "TFF2 polypeptide" are used interchangeably and refer to a class of polypeptides having an amino acid sequence as set forth in SEQ ID NO: 1 (human origin) or SEQ ID NO: 2 (murine origin) or homologous sequences thereof. The term may include TFF2 polypeptides of various mammalian origins, e.g., TFF2 polypeptides derived from human, mouse, rat, and the like. The homology between TFF2 proteins can be higher than or equal to 80%, higher than or equal to 85%, higher than or equal to 90%, higher than or equal to 95%, higher than or equal to 96%, higher than or equal to 97%, higher than or equal to 98%, higher than or equal to 99%, or equal to 100%.

As used herein, the terms "TFF2-encoding nucleic acid molecule", "TFF2-encoding sequence", or "TFF2 gene" are used interchangeably, and all refer to a sequence encoding a TFF2 protein or polypeptide described herein. The nucleic acid molecule can be selected from, for example, the sequence of SEQ ID NO: 3 (full-length human sequence), the sequence of SEQ ID NO: 4 (human cDNA sequence), the sequence of SEQ ID NO: 5 (full-length mouse sequence), the sequence of SEQ ID NO: 6 (mouse cDNA sequence), a molecule that hybridizes with any of these sequences under a stringent condition, or family gene molecules that are highly homologous to the above-mentioned molecules. The expression of the gene has certain regulating effect on the occurrence and influence of inflammation.

As used herein, the term "stringent conditions" refers to: (1) hybridization and elution at lower ionic strength and higher temperature, such as 0.2×SSC, 0.1% SDS, 60° C.; or (2) hybridization under the presence of denaturing agents, such as 50% (v/v) formamide, 0.1% calf serum/0.1% Ficoll, 42° C., etc.; or (3) hybridization that occurs only if the two sequences are at least 50%, preferably 55% or more, 60% or more, 65% or more, 70% or more, 75% or more, 80% or more, 85% or more, or 90% or more, more preferably 95% or more identical. For example, the sequence may be the complement of the sequence defined in (a).

The full-length nucleotide sequence of the TFF2 gene of the present disclosure or a fragment thereof can usually be obtained by PCR amplification, recombination or artificial synthesis. For example, for PCR amplification, primers can be designed, for example, based on the relevant nucleotide sequences, especially open reading frame sequences, disclosed in the present disclosure or in other databases, and, commercially available cDNA libraries or a cDNA library prepared by using conventional methods known by those skilled in the art can be used as a template to amplify the relevant sequences. When the sequence is long, it is often necessary to perform two or more rounds of PCR amplification, and then the amplified fragments can be spliced together in the correct order.

It should be understood that the TFF2-encoding nucleic acid of the present disclosure can be obtained from humans, and other genes that are obtained from other animals and are highly homologous to the human TFF2 gene (such as with 70% or more, 75% or more, 80% or more, 85% or more, 90% or more, 95% or more, 96% or more, 97% or more, 98% or more, 99% or more sequence identity) are also within the scope of equivalence contemplated by the present disclosure. Methods and tools for aligning sequence identity, such as BLAST, are also well known in the art.

The TFF2 protein of the present disclosure can be a protein encoded by the aforementioned encoding nucleic acid molecules (e.g., the encoding nucleic acid molecules of SEQ ID NOs: 3-6) or a homologous sequence of these proteins with an anti-inflammatory effect (e.g., those TFF2 homologous sequences that can be obtained via databases or alignment softwares known in the art), variants or modified forms thereof. For example, the TFF2 protein can be selected from: (a) the amino acid sequence set forth in SEQ ID NO: 1 or SEQ ID NO: 2; or (b) a protein or polypeptide derived from (a) with substitution, deletion or addition of one or more residues in the amino acid sequence defined in (a) and with an anti-inflammatory activity.

Variant forms of the proteins or polypeptides of the present disclosure include (but are not limited to): those having deletion, insertion and/or substitution of one or more (usually 1-50, preferably 1-30, more preferably 1-20, and most preferably 1-10, for example 1, 2, 3, 4, 5, 6, 7, 8, 9 or 10) amino acid residues, and those having addition of one or several (usually within 20, preferably within 10, more preferably within 5) amino acids at C-terminal and/or N-terminal. For example, in the art, substitution with amino acids of similar or close properties generally does not alter the function of a protein or polypeptide. As another example, the addition of one or several amino acids to the C-terminus and/or N-terminus generally does not alter the function of the protein or polypeptide. For example, the TFF2 protein or polypeptide of the present disclosure may or may not include an initial methionine residue and still has the activity of regulating inflammation.

Depending on the host used in the recombinant production protocol, the proteins or polypeptides of the present disclosure may be glycosylated, or may be non-glycosylated. The term also includes active fragments and active derivatives of the TFF2 protein.

Variant forms of the polypeptide include: homologous sequences, conservative variants, allelic variants, natural mutants, induced mutants, and proteins that are encoded by sequences that hybridize to the TFF2 protein-encoding sequence under high or low stringency conditions, and polypeptides or proteins obtained using antiserum against TFF2 protein.

Interferon-κ Protein (IFN-κ Protein)

IFN-κ consists of 207 amino acids with a molecular weight of about 25 kD, including a signal peptide of 27 amino acids at the N-terminal. It belongs to the same type 1 interferon family as IFN-α and IFN-β, and is a more conservative and ancient type 1 interferon. IFN-κ is mainly expressed in epithelial keratinocytes and it transmits downstream signals through IFNAR1 and IFNAR2, activates ISGs and exerts antiviral effect.

As used herein, the terms "interferon-κ protein", "IFN-κ polypeptide" and "IFN-κ protein" are used interchangeably and refer to a class of polypeptides having the amino acid sequence as set forth in SEQ ID NO: 7 (human origin) or SEQ ID NO: 8 (murine origin) or a homologous sequence thereof. The term may include IFN-κ polypeptides of various mammalian origins, e.g., IFN-κ polypeptides derived from humans, mice, rats, and the like. The homology between IFN-κ proteins can be higher than or equal to 80%, higher than or equal to 85%, higher than or equal to 90%, higher than or equal to 95%, higher than or equal to 96%, higher than or equal to 97%, higher than or equal to 98%, higher than or equal to 99%, or equal to 100%.

As used herein, the terms "IFN-κ encoding nucleic acid molecule", "IFN-κ encoding sequence" or "IFN-κ gene" are used interchangeably, and all refer to sequences encoding IFN-κ proteins or polypeptides described in the present disclosure. The nucleic acid molecule can be selected from, for example, the sequence of SEQ ID NO: 9 (full-length human sequence), the sequence of SEQ ID NO: 10 (human cDNA sequence), the sequence of SEQ ID NO: 11 (full-length mouse sequence), the sequence of SEQ ID NO: 12 (mouse cDNA sequence), a molecule that hybridizes with these sequences under stringent conditions (such as those stringent conditions described above), or family gene molecules with high homology to the above-mentioned molecules. The expression of said genes can activate ISGs and exert antiviral effects.

The full-length nucleotide sequence of the IFN-κ gene of the present disclosure or a fragment thereof can usually be obtained by PCR amplification, recombination or artificial synthesis. For example, for PCR amplification, primers can be designed, for example, based on the relevant nucleotide sequences, especially open reading frame sequences, disclosed in the present disclosure or in other databases, and, commercially available cDNA libraries or a cDNA library prepared by using conventional methods known by those skilled in the art can be used as a template to amplify the relevant sequences. When the sequence is long, it is often necessary to perform two or more rounds of PCR amplification, and then the amplified fragments can be spliced together in the correct order.

It should be understood that the IFN-κ encoding nucleic acid of the present disclosure can be obtained from humans, and other genes that are obtained from other animals and are highly homologous to the human IFN-κ gene (such as with 70% or more, 75% or more, 80% or more, 85% or more, 90% or more, 95% or more, 96% or more, 97% or more, 98% or more, 99% or more sequence identity) are also within the scope of equivalence contemplated by the present disclosure. Methods and tools for aligning sequence identity, such as BLAST, are also well known in the art.

The IFN-κ protein of the present disclosure can be the protein encoded by the aforementioned nucleic acid molecules (e.g., the encoding nucleic acid molecules of SEQ ID NOs: 9 to 12) or the homologous sequences of these proteins with an anti-inflammatory effect (e.g., those IFN-κ homologous sequences that can be obtained via databases or alignment softwares known in the art), variants or modified forms thereof. For example, the IFN-κ protein can be selected from: (a) the amino acid sequence set forth in SEQ ID NO: 7 or SEQ ID NO: 8; or (b) an protein or polypeptide derived from (a) with substitution, deletion or addition of one or more residues in the amino acid sequence defined in (a) and with an anti-inflammatory activity.

Variant forms of the proteins or polypeptides of the present disclosure include (but are not limited to): those having deletion, insertion and/or substitution of one or more (usually 1-50, preferably 1-30, more preferably 1-20, and most preferably 1-10, for example 1, 2, 3, 4, 5, 6, 7, 8, 9 or 10) amino acid residues, and those having addition of one or several (usually within 20, preferably within 10, more preferably within 5) amino acids at C-terminal and/or N-terminal. For example, in the art, substitution with amino acids of similar or close properties generally does not alter the function of a protein or polypeptide. As another example, the addition of one or several amino acids to the C-terminus and/or N-terminus generally does not alter the function of the protein or polypeptide. For example, the IFN-κ protein or polypeptide of the present disclosure may or may not include an initial methionine residue and still has the activity of inhibiting inflammatory factors.

Depending on the host used in the recombinant production protocol, the proteins or polypeptides of the present disclosure may be glycosylated, or may be non-glycosylated. The term also includes active fragments and active derivatives of the IFN-κ protein.

Variant forms of the polypeptide include: homologous sequences, conservative variants, allelic variants, natural mutants, induced mutants, and proteins that are encoded by sequences that hybridize to the IFN-κ protein-encoding sequence under high or low stringency conditions, and polypeptides or proteins obtained using antiserum against IFN-κ protein.

Application Against Novel Coronavirus Infection

As used herein, the term "treating" includes: (1) preventing or delaying the onset of clinical symptoms of a disease, disorder or condition in an animal (especially a mammal and in particular humans); (2) inhibiting the disease, disorder or condition (e.g. arresting, alleviating or delaying the progression of the disease or its recurrence (in the case of maintenance therapy), or at least one of its clinical or subclinical symptoms); and/or (3) alleviating the disease (i.e. causing regression of the disease, disorder or condition or at least one of its clinical or subclinical symptoms). The benefit to the treated patient is statistically significant or at least perceptible by the patient or by the physician.

In some embodiments, a combination comprising a TFF2 protein and an IFN-κ protein is effective in alleviating novel coronavirus infection and related conditions, such as novel coronavirus pneumonia and its symptoms. In one embodiment, the symptoms are those such as dyspnea, hypoxemia, acute respiratory distress syndrome, septic shock, metabolic acidosis, coagulopathy, multiple organ failure, fever, dry cough, fatigue, nasal congestion, runny nose, sore throat, myalgia, and diarrhea.

In some embodiments, the combination of TFF2 protein and IFN-κ protein of the present disclosure can be used to treat various clinical types of novel coronavirus pneumonia, such as mild, common, serious, and critical types of novel coronavirus pneumonia.

Combinations of TFF2 Protein and IFN-κ Protein and Products

The present disclosure provides a combination comprising a therapeutically effective amount of TFF2 protein and IFN-κ protein, and optionally a pharmaceutically acceptable carrier. In some embodiments of the present disclosure, the combination is useful for the treatment of novel coronavirus infection and related conditions. In some embodiments of the present disclosure, the combination may be a pharmaceutical composition, a formulation combination, a kit, or a combination in use.

As used herein, the term "pharmaceutical composition" refers to a pharmaceutical combination comprising both TFF2 protein and IFN-κ protein. As used herein, the term "combination formulation", "combined formulation" or "kit" means that TFF2 protein and IFN-κ protein can be administered independently, in separate forms or by using different fixed combinations with separate amounts of the active ingredients. In combinations, the ratio of the amount of IFN-κ protein to be administered relative to the amount of TFF2 protein can vary, for example, to meet the needs of a subgroup of subjects to be treated or the needs of an individual subject, which vary by age, sex, weight of the subject, etc. Different parts of the kit can be administered at the same time or chronologically staggered, e.g., at different time points and at the same or different time intervals for any part of the kit. Thus, the present disclosure relates to combinations (e.g., a combined formulation or pharmaceutical composition) of TFF2 protein and IFN-κ protein that are to be administrated simultaneously, separately or sequentially.

The combination can also be used in an add-on therapy. As used herein, "add-on" or "add-on therapy" refers to a set of agents used in a therapy in which a subject receiving such therapy, after initiating a first treatment regimen of one or more agents, begins receiving a second treatment regimen of one or more different agents in addition to the first treatment regimen, so not all agents used in this therapy are administrated at the same time. For example, additional IFN-κ protein therapy can be administered to patients already receiving TFF2 protein therapy, or vice versa.

In some embodiments, the actives in the combinations or products of the present disclosure include TFF2 protein and IFN-κ protein. In some embodiments, the actives in the combinations or products of the present disclosure essentially consist of TFF2 protein and IFN-κ protein, or consist of TFF2 protein and IFN-κ protein.

As used herein, the terms "comprising" or "including" include "containing", "consisting essentially of", and "composed of". As used herein, the term "pharmaceutically acceptable" ingredient is one that is suitable for use in humans and/or animals without undue adverse side effects (e.g., toxicity, irritation, and allergy), i.e., a substance with a reasonable benefit/risk ratio. As used herein, the term "effective amount" refers to an amount that produces function or activity in humans and/or animals and is acceptable to humans and/or animals.

The active ingredients in the combination or product of the present disclosure account for 0.01 to 100 wt % of the total weight of the formulation or composition, and the balance is pharmaceutically acceptable carriers and other additives, etc. For example, when the formulation or composition is a solution containing an active protein, the active protein may account for 0.01 to 10 wt % of the total weight; when the formulation or composition is in the form of a powder, it may substantially or completely consist of the active protein.

In some embodiments, the active ingredients in the combination or product of the present disclosure are present in amounts that produce excellent or synergistic therapeutic effects. The excellent therapeutic effect includes, but is not limited to, significantly shortened time required for remission of the disease, such as significantly reduced time to radiographic improvement, significantly reduced time to cough resolution and/or reduced length of hospital stay for a patient, compared with treatment with a therapeutically effective amount of hydroxychloroquine (such as a dose of 100 mg orally once a day).

In some embodiments, the amount of TFF2 protein in the combination or product of the present disclosure ranges from 0.1 to 100 mg, from 0.5 to 50 mg, from 1 to 40 mg, or from 5 to 30 mg. In some embodiments, the amount of IFN-κ protein in the combination of the present disclosure ranges from 0.01 to 100 mg, from 0.05 to 80 mg, from 0.1 to 70 mg, from 0.5 to 50 mg. In some embodiments, the amount of IFN-κ protein is from $1\times10^4$ to $1\times10^8$ active units, from $5\times10^4$ to $5\times10^7$ active units, from $1\times10^5$ to $1\times10^7$ active units, or from $5\times10^5$ to $5\times10^6$ active units.

In some embodiments, the mass ratio of TFF2 protein to IFN-κ protein in the combination or product of the present disclosure is from 1:100 to 100:1, from 1:50 to 50:1, from 1:10 to 10:1, from 1:5 to 5:1, from 1:2 to 2.5:1, or from 1:1 to 2:1.

As used herein, the term "pharmaceutically acceptable carrier" refers to a carrier for administration of a therapeutic agent, including various excipients and diluents. The term refers to pharmaceutical carriers which are not themselves essential active ingredients and which are not unduly toxic after administration. Suitable carriers are well known to those of ordinary skill in the art. A full discussion of pharmaceutically acceptable excipients can be found in Remington's Pharmaceutical Sciences (Mack Pub. Co., NJ 1991).

Pharmaceutically acceptable carriers in the formulation combination, pharmaceutical composition or kit may contain liquids such as water, saline, glycerol and ethanol. In addition, auxiliary substances such as fillers, disintegrating agents, lubricants, glidants, effervescent agents, wetting or emulsifying agents, flavoring agents, pH buffering substances and the like may also be present in these carriers. Generally, these materials can be formulated in a non-toxic, inert, and pharmaceutically acceptable aqueous carrier medium, usually at a pH of about 5-8, preferably at a pH of about 6-8.

As used herein, the term "unit dosage form" refers to the preparation of the compositions of the present disclosure into dosage forms required for a single administration for convenience of administration, including but not limited to various solids (e.g., powders), liquids, aerosols tablets, capsules, sustained-release formulations.

In another preferred embodiment of the present disclosure, the composition is in unit dosage form or multi-dosage form, and wherein the amount of TFF2 protein ranges from 0.1 to 100 mg/dose, from 0.5 to 50 mg/dose, from 1 to 40 mg/dose, or from 5 to 30 mg/dose; the amount of IFN-κ protein ranges from 0.01 to 100 mg/dose, from 0.05 to 80 mg/dose, from 0.1 to 70 mg/dose, or from 0.5 to 50 mg/dose. Alternatively, the amount of the IFN-κ protein ranges from $1\times10^4$ to $1\times10^8$ active units/dose, from $5\times10^4$ to $5\times10^7$ active units/dose, from $1\times10^5$ to $1\times10^7$ active units/dose, or from $5\times10^5$ to $5\times10^6$ active units/dose.

In some embodiments of the present disclosure, a subject may be administered one or more active ingredients of the present disclosure as needed, e.g., from 1 to 6 doses, from 1 to 3 doses, or 1 dose of a product of the present disclosure daily, every two days, every three days, or weekly.

It will be understood that the effective dose of the active agent employed may vary depending on the severity of the subject to be administered or treated. The specific situation is determined according to the individual conditions of the subject (e.g., the subject's weight, age, physical condition, and desired effect), which is within the judgment of a skilled physician.

The routes of administration of the medicaments or pharmaceutical compositions or kits of the present disclosure may include, but are not limited to, one or more of the following: inhalation, intranasal, topical administration, targeted administration to target tissues, injection, oral administration, and the like. The TFF2 protein and the IFN-κ protein or formulations or compositions comprising the proteins can be administered simultaneously or separately in the same or different ways.

Compared with monotherapy using sole active, administration of a combination comprising TFF2 protein and IFN-κ protein results in a beneficial effect, e.g. synergistic, therapeutic effect, or other unexpected beneficial effect, e.g. significantly better efficacy, fewer and/or milder side effects than the existing drugs.

A combination comprising TFF2 protein and IFN-κ protein, in subeffective doses of TFF2 protein and IFN-κ protein, can achieve the same effect as an effective dose of any of the individual compounds. Lower doses of TFF2 protein and IFN-κ protein can be used compared to monotherapy using only IFN-κ protein or TFF2 protein. For example, not only can the dose used be smaller, but it can also be used less frequently. Furthermore, the occurrence of side effects can be reduced, and/or the response rate to IFN-κ protein or TFF2 protein-based therapy can be increased. All are consistent with the expectations and requirements of the patient to be treated.

In some embodiments, known clinical classification methods and indicators can be used to judge the curative effect of the combination of the present disclosure. For example, reference can be made to "Novel Coronavirus Pneumonia Diagnosis and Treatment Plan (Provisional 7th Edition)". In some embodiments, the combination of TFF2 protein and IFN-κ protein reduces the incidence, and severity, and shortens the course of treatment, etc. of a disease or symptom.

EXAMPLES

The present disclosure will be further described below with reference to particular examples. It should be understood that these examples are only used to illustrate the present disclosure and not to limit the scope of the present disclosure. Appropriate modifications and variations can be made to the present disclosure by those skilled in the art, and these modifications and variations are all within the scope of the present disclosure.

The experimental method of unspecified conditions in the following examples, can adopt the conventional method in this area, for example with reference to "Molecular Cloning: A Laboratory Manual (Third Edition)" (New York: Cold Spring Harbor Laboratory Press, 1989) or as suggested by the supplier. DNA sequencing methods are routine methods in the art, and corresponding tests can also be provided by commercial companies.

Percentages and parts are by weight unless otherwise indicated. Unless otherwise defined, all professional and scientific terms used herein have the same meanings as those familiar to those skilled in the art. In addition, any method and material similar or equivalent to those described can be used in the methods of the present disclosure. Methods and materials for preferred embodiments described herein are provided for illustrative purposes only.

Example 1. Expression and Purification of TFF2 Protein

Step 1: Recombinant Human TFF2 Protein Preparation Protocol Optimization

Gene was cloned according to the TFF2 sequence, and the recombinant pSV1.0-TFF2 plasmid was transfected into 293T cells. Then the eukaryotic expression of TFF2 protein was detected by WB, and eluted with imidazole with different concentration gradients through a nickel column. The target protein was collected, filtered, washed, to obtain high-purity TFF2 protein. The specific steps were as follows:

PCR amplification was performed using the cDNA generated by reverse transcription of RNA extracted from H9N2-infected mouse lung tissue as a template:

```
Upstream primer (SEQ ID NO: 13):
5'-CGCTCTAGAATGCGACCTCGAGGTGCCCC-3',

Downstream primer (SEQ ID NO: 14):
5'-CCTGGATCCTCAGTAGTGACAATCTTCCA-3'.
```

The amplification procedure was: pre-denaturation at 95° C. for 2 minutes; denaturation at 95° C. for 15 seconds; annealing at 55° C. for 30 seconds; extension at 72° C. for 30 seconds; final extension at 72° C. for 10 minutes; the number of cycles was 30. After the amplification, the target gene was separated on a 1% agarose gel, and the amplified product TFF2 was recovered using the Sanprep Column DNA Gel Recovery Kit. The recovered product of TFF2 and the vector pSV1.0 were recovered by double digestion with endonucleases BamHI and XbaI. Digestion was carried out in a water bath at 37° C. for 7 hours, followed by 1% agarose gel electrophoresis using Sanprep Column DNA Gel Recovery Kit to recover the fragments. The target fragment TFF2 was ligated with vector pSV1.0 overnight at 4° C. to form a recombinant plasmid pSV1.0-TFF2. The recombinant plasmid was transformed into *Escherichia coli E. coli* TOP10, and positive clones were identified by colony PCR and double restriction digestion (BamHI, XbaI). The target sequence was confirmed by sequencing to be completely correct with no mutation.

The recombinant plasmid pSV1.0-TFF2 verified by sequencing was transfected into 293FT cells. The transfection reagent was TurboFect. The medium was DMEM complete medium (10% FBS and 1% PS). The cells were cultured at 37° C. for 72 hours and then removed and collected into pre-cooled EP tubes, lysed with RIPA lysis buffer. 5×SDS loading buffer was added to the supernatant, heated in a boiling water bath for 10 minutes to denature the protein, and then the supernatant was centrifuged for 10 minutes, as a spotting sample. Then, the proteins were separated by SDS-polyacrylamide gel electrophoresis (SDS-PAGE) at a separating gel concentration of 15%, a voltage of electrophoresis of 70V, and the running time was 30-40 minutes (started at the initial separation of marker). After the bromophenol blue migrated out of the indicated position in stacking gel, the voltage was adjusted to 110V, and the power was turned off after an hour and a half, and the membrane transfer was carried out with a constant current of 200 mA for 1.5 hours. After the membrane transfer, the PVDF front membrane (the side in contact with the gel) was marked and placed in 5% nonfat milk for 1 hour at room temperature for blocking. The primary antibody was added at appropriate dilution ratio (TFF2:1:400 or β-actin:1:1000) diluted with 5% nonfat milk, and incubated overnight at 4° C. on a shaker. After washing the membrane with 0.05% PBST, the secondary antibodies, TFF2-goat anti-rabbit (1:3000); β-actin-goat anti-mouse (1:3000) were added, diluted with 5% nonfat milk, and incubated on a shaker at room temperature for 1 hour. The membrane was washed, and developed. The membrane was exposed using a quantitative analyzer for 2 minutes, and the development results were recorded and analyzed.

The results showed that the cells expressed a large amount of TFF2 protein, which was secreted into the cell supernatant, and after concentration, TFF2 protein was not contained in the filtered waste fluid. In order to quantify the concentration of TFF2, a standard curve of TFF2 was made using the SEA748MU ELISA kit for TFF2 purchased from USCN, and the concentration of TFF2 was quantified according to the optical density (OD) value of the standard.

Step 2: Preparation of Recombinant Human TFF2 Protein

On the basis of step 1, the amplification preparation was carried out, and the cells were harvested after transfecting HEK293 cells for 5 days, and the protein expression was detected by SDS-PAGE.

The secreted supernatant was harvested, purified by hydrophobic column and ion column purification steps to obtain qualified protein products. Qualified protein products met the following quality standards: protein concentration ≥0.5 mg/mL, protein purity >95%, endotoxin <100 Eu/mg, protein preservation solution: PBS, pH 7.4.

The entire scale-up preparation process was produced according to GMP standards.

Figure 1B:
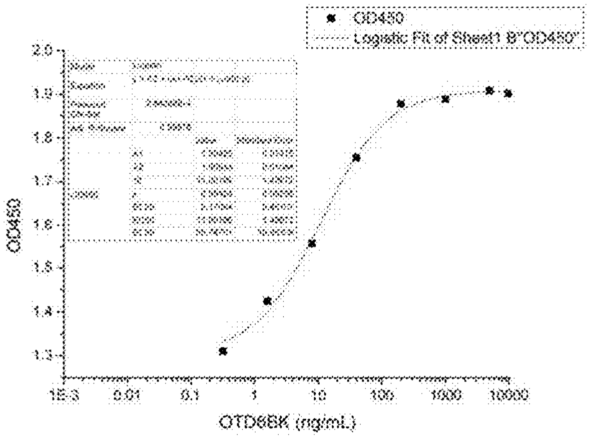
FIG. 1B: Functional activity test of TFF2 protein: OD450 logistic fit curve of in vitro proliferation of MCF7 cells stimulated with TFF protein.

Upon SDS-PAGE electrophoresis and Coomassie brilliant blue staining, the prepared TFF2 protein was identified to have a purity >95%, and was transported in place at low temperature in the form of lyophilized powder. It was verified by using in vitro cell lines to be able to stimulate the proliferation of MCF7 cells, with a median effective dose of 11 ng/mL (as shown in FIG. 1).

TFF2 Protein Amino Acid Sequence

The amino acid sequence of the obtained TFF2 protein is shown below (SEQ ID NO: 1):

```
EKPSPCQCSRLSPHNRTNCGFPGITSDQCFDNGCCFDSSVTGVPWCFHP
LPKQESDQCVMEVSDRRNCGYPGISPEECASRKCCFSNFIFEVPWCFFP
KSVEDCHY
```

Example 2. Expression and Purification of IFN-κ Protein

Step 1: Recombinant Human IFN-κ Protein Preparation Protocol Optimization

IFN-κ was obtained by cloning from the human genome. The nucleotide sequence of the encoding gene is set forth in SEQ ID NO: 1, and the full-length amino acid sequence is set forth in SEQ ID NO: 2. The IFN-κ belongs to type I interferon family, which shares only 30% homology with IFN-α and IFN-β.

The eukaryotic expression vector of IFN-κ was constructed, and the mature secreted protein was expressed in eukaryotic cell lines in vitro. The IFN-κ eukaryotic expression plasmid was constructed using the eukaryotic expression vector pSV1.0. The construction method was as follows: The cDNA generated by reverse transcription of RNA extracted from A549 cells was used as a template, and the corresponding primers were used for PCR amplification.

```
Upstream primer (SEQ ID NO: 15):
5'-CGCTCTAGA ATGAGCACCAAACCTG-3',

Downstream primer (SEQ ID NO: 16):
5'-TCTGGATCCTTATTTCCTCCTGAA-3'.
```

PCR reaction procedure: 95° C., 2 minutes; 35 cycles of: 95° C., 15 seconds, 55° C., 30 seconds, 72° C., 30 seconds; 72° C., 10 minutes; 4° C., 30 minutes.

After the amplification, the target gene was separated in a 1% agarose gel, and the gel was cut and recovered. Sanprep Column DNA Gel Recovery Kit was used to recover the PCR fragments. The recovered IFN-κ product and the pSV1.0 vector were subjected to double digestion with BamHI and XbaI, and then T4 DNA ligase was used to ligate the fragment and vector overnight at 4° C. The ligation product was transformed into *E. coli* TOP10 cells on the next day, which were cultured in kanamycin-containing culture plates overnight. On the third day, a single colony was randomly picked for PCR identification, and positive clones were selected for double-enzyme digestion identification. The IFN-κ gene was successfully cloned after sequencing and mutation site correction to verify that the entire sequence was correct. The cells transfected with pSV1.0-IFN-κ plasmid and supernatants thereof were collected and identified by Western blotting (WB). It was found that IFN-κ was expressed in both cells and supernatants.

Step 2: Preparation of Recombinant Human IFN-κ Protein

On the basis of step 1, the amplification preparation was carried out, and the protein expression was detected by SDS-PAGE.

The inclusion bodies were harvested for renaturation, and purified by hydrophobic column, ion-exchange column and other purification steps to obtain qualified renatured protein products.

Qualified protein products met the following quality standards: protein concentration ≥1 mg/mL, protein purity >95%, endotoxin <100 Eu/mg, protein preservation solution: PBS, pH7.4.

The entire scale-up preparation process was produced according to GMP standards.

Figure 2A:
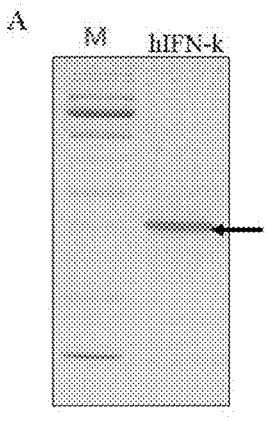
FIG. 2A: SDS-PAGE electropherogram of IFN-κ protein.
Figure 2B:
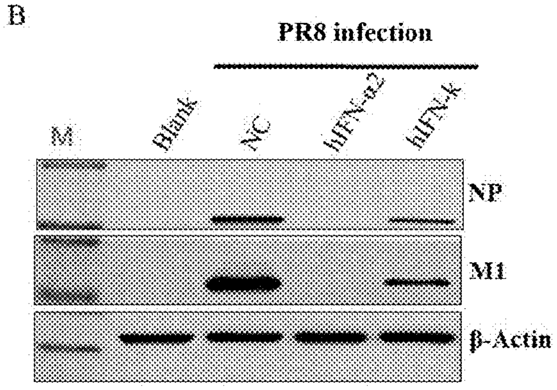
FIG. 2B: In vitro functional activity assay of IFN-κ protein: IFN-κ protein inhibited the replication of influenza virus PR8 in A549 cell line.
Figure 3:
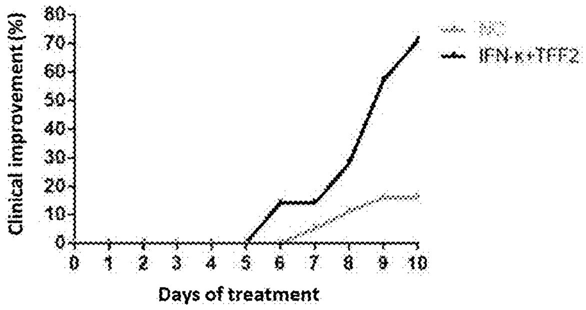
FIG. 3: The percentage of patients with novel coronavirus having clinical improvement upon combined administration of TFF2 protein and IFN-κ protein.
Figure 4:
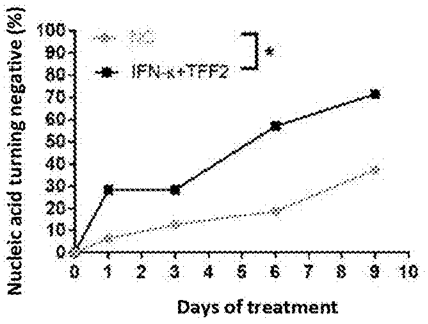
FIG. 4: The percentage of patients with novel coronavirus whose nucleic acid turned negative upon the combined administration of TFF2 protein and IFN-κ protein.
Figure 5:
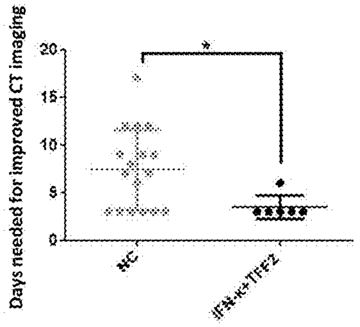
FIG. 5: Days required for CT imaging improvement in patients with novel coronavirus upon the combined administration of TFF2 protein and IFN-κ protein.
Figure 6:
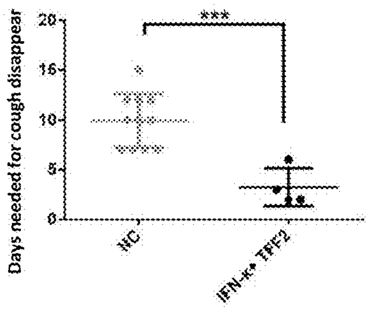
FIG. 6: The number of days required for the cough to disappear in patients with novel coronavirus upon the combined administration of TFF2 protein and IFN-κ protein.
Figure 7:
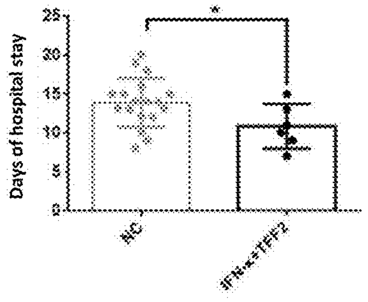
FIG. 7: The effect of the combined administration of TFF2 protein and IFN-κ protein on the length of hospital stay in patients with novel coronavirus.
Figure 8:
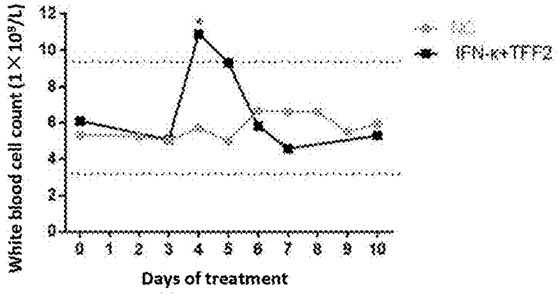
FIG. 8: The effect of the combined administration of TFF2 protein and IFN-κ protein on white blood cell count in patients with novel coronavirus.
Figure 9:
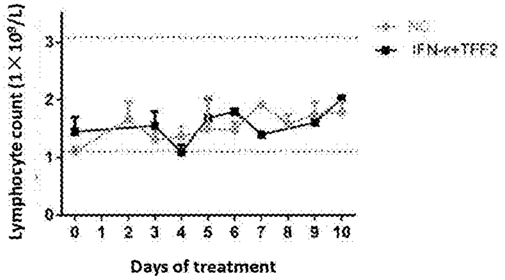
FIG. 9: The effect of the combined administration of TFF2 protein and IFN-κ protein on lymphocyte count in patients with novel coronavirus.
Figure 10:
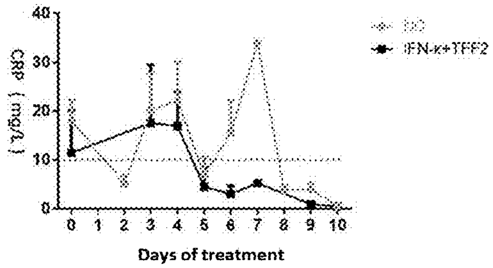
FIG. 10: The effect of the combined administration of TFF2 protein and IFN-κ protein on C-reactive protein (CRP) in patients with novel coronavirus.
Figure 11:
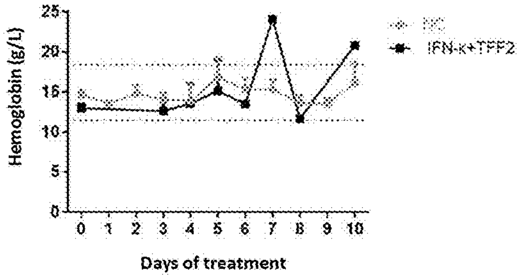
FIG. 11: The effect of the combined administration of TFF2 protein and IFN-κ protein on hemoglobin in patients with novel coronavirus.
Figure 12:
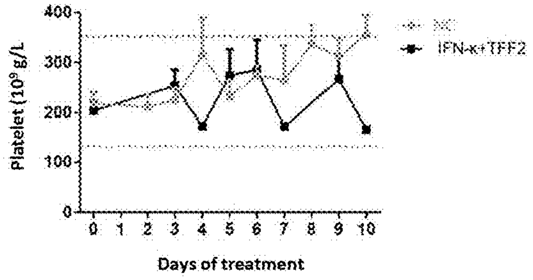
FIG. 12: The effect of the combined administration of TFF2 protein and IFN-κ protein on platelet count in patients with novel coronavirus.

Upon SDS-PAGE electrophoresis and Coomassie brilliant blue staining, the protein prepared by above method was identified to have purity >95%, and it was transported in place in the form of lyophilized powder at low temperature. After activity determination by WISH-VSV method, its specific activity was $1.16\times10^6$ U/mg. We further verified that purified IFN-κ protein could inhibit the replication of influenza virus PR8 in A549 cell line (as shown in FIG. 2).

IFN-κ Protein Amino Acid Sequence

The amino acid sequence of the obtained IFN-κ protein is shown below (SEQ ID NO: 7):

```
MLDCNLLNVHLRRVTWQNLRHLSSMSNSFPVECLRENIAFELPQEFLQY

TQPMKRDIKKAFYEMSLQAFNIFSQHTFKYWKERHLKQIQIGLDQQAEY

LNQCLEEDKNENEDMKEMKENEMKPSEARVPQLSSLELRRYFHRIDNFL

KEKKYSDCAWEIVRVEIRRCLYYFYKFTALFRRK
```

Example 3. Preparation of TFF2 Protein and IFN-κ Protein Formulation

The TFF2 protein and IFN-κ protein produced according to the GMP standard in Example 1 and Example 2 were freshly prepared. 5 mg TFF2 protein and 2 mg IFN-κ protein were mixed, or 5 mg TFF2 protein and 1 mg IFN-κ protein were mixed, or 2 mg of TFF2 protein and 1 mg of IFN-κ protein were mixed, using sterile water for injection, to make a 5 mL solution, which was placed into a sterile reagent bottle, and stored at 4° C., ready for use.

Example 4. Efficacy and Safety Study of TFF2 Protein Combined with IFN-κ Protein in the Treatment of Patients with Novel Coronavirus This clinical study was approved by the Ethics Committee of the Shanghai Public Health Clinical Center for ethics review. The enrolled patients were recruited by the Shanghai Public Health Clinical Center, and all signed informed consent.

Patient Enrollment Criteria

1. Age: 18-70 years old; gender: not limited;
2. In line with the clinical diagnosis of viral pneumonia: fever; normal or low white blood cells, with or without thrombocytopenia; infiltration shadows on chest imaging;
3. Positive for the etiology of the novel coronavirus;
4. Able to receive aerosol inhalation administration;
5. Agree to sign a written Informed Consent Form before the start of the study.

Patient Exclusion Criteria

1. There was other evidence of pneumonia caused by non-novel coronavirus;
2. There was clear evidence of bacterial infection;

3. Subjects who have used antiviral drugs within one week before screening and who may need another antiviral treatment during the study;
4. There are serious non-infectious pulmonary underlying diseases, including: pulmonary tuberculosis, pulmonary edema, pulmonary embolism;
5. Severe liver and kidney dysfunction;
6. Being involved in or having been involved in other clinical studies within 30 days before administration;
7. Having a history of allergy to interferon;
8. Pregnant women (positive urine or serum pregnancy test) or lactating women;
9. Any condition that the investigators believed may not be suitable for enrollment in this trial, or may increase the risk of subjects or interfere with clinical trials.

Basic Information of Subjects Involved and Treatment Methods for the Research

Information about the subjects involved:

| Patient No. | Gender | Age | Clinical Classification | Treatment |
|---|---|---|---|---|
| Experimental group: (n = 6) aerosol inhalation ×3 times | | | | |
| M1-LJP | Male | 50 | Normal type | Standard treatment + (5 mg TFF2 + 1 mg IFN-κ) |
| M2-WP | Male | 45 | Normal type | Standard treatment + (5 mg TFF2 + 1 mg IFN-κ) |
| M3-WR | Female | 52 | Normal type | Standard treatment + (5 mg TFF2 + 1 mg IFN-κ) |
| M4-LFY | Female | 68 | Normal type | Standard treatment + (5 mg TFF2 + 1 mg IFN-κ) |
| M5-ZMJ | Female | 30 | Normal type | Standard treatment + (5 mg TFF2 + 1 mg IFN-κ) |
| M6-LYM | Male | 53 | Normal type | Standard treatment + (5 mg TFF2 + 1 mg IFN-κ) |
| Control group: (n = 18) | | | | |
| C1-XGZ | Male | 48 | Normal type | Standard treatment |
| C2-WJS | Male | 56 | Normal type | Standard treatment |
| C3-WTX | Female | 67 | Normal type | Standard treatment |
| C4-YJP | Female | 58 | Normal type | Standard treatment |
| C5-GXY | Female | 37 | Normal type | Standard treatment |
| C6-CXH | Female | 57 | Normal type | Standard treatment |
| C7-CQ | Female | 68 | Normal type | Standard treatment |
| C8-LCY | Male | 62 | Normal type | Standard treatment |
| C9-LXF | Female | 60 | Normal type | Standard treatment |
| C10-PLM | Female | 67 | Normal type | Standard treatment |
| C11-XXH | Female | 60 | Normal type | Standard treatment |
| C12-ZXY | Female | 57 | Normal type | Standard treatment |
| C13-CXD | Male | 41 | Normal type | Standard treatment |
| C14-JJS | Male | 66 | Normal type | Standard treatment |
| C15-YZQ | Male | 67 | Normal type | Standard treatment |
| C16-YDS | Male | 62 | Normal type | Standard treatment |
| C17-JM | Male | 59 | Normal type | Standard treatment |
| C18-LJH | Female | 55 | Normal type | Standard treatment |

Specific Mode of Administration

Control group: The standard treatment was administrated, and the drugs used included hydroxychloroquine (i.e., hydroxychloroquine sulfate tablets), Lianhua Qingwen capsules, and other treatment medicines and methods recommended in the "Novel Coronavirus Pneumonia Diagnosis and Treatment Plan (Provisional 6$^{th}$ Edition)".

Experimental group: Based on conventional drug treatment, the patients received 5 mg TFF2 protein and 1 mg IFN-κ protein inhalation therapy on Day 2, 4 and 6 after enrollment. The 5:1 formulation prepared in Example 3 was poured into the atomizing cup, and the patient was subjected to aerosol inhalation for 20-30 minutes using an atomizing generator with a particle size of <5 um.

Evaluation Indicators

| Effectiveness evaluation 1 | Effectiveness evaluation 2 | Safety indicators |
|---|---|---|
| Clinical response rate | White blood cell count | Alanine aminotransferase (ALT) |
| Time to viral nucleic acid turning negative | C-reactive protein (CRP) | Aspartate aminotransferase (AST) |
| Time to chest imaging (CT) improvement | Hemoglobin | Creatinine |
| Hospital stay | Platelets | |
| Time to cough relief | Absolute value of lymphocytes | |

Clinical Study Results

The results of the effectiveness study are shown in FIGS. 3-12. The results show that the use of IFN-k+TFF2 protein combined with aerosol inhalation in the treatment of patients with COVID-19 has obvious clinical benefits, and can improve the clinical symptoms of patients, reduce the time for nucleic acid turning negative, restore lung function more quickly, significantly improve the lung conditions detected by CT imaging, reduce the duration of hospital stay, shorten the time it takes for cough to disappear, rapidly increase white blood cells, and reduce the CRP response, indicating the reduced production of inflammatory stress proteins and a certain clinical effect.

In addition, the trial results show that the ALT and AST levels of the aerosol treatment group were lower than those of the standard treatment group, indicating that the aerosol inhalation does not damage the liver. The levels of blood cells, platelets and hemoglobin were similar, indicating that the aerosol inhalation treatment is also safe for blood function.

Conclusion of the Study

The results of clinical trials show that the combined treatment of TFF2 protein and IFN-κ protein can improve the symptoms of clinical patients, accelerate the nucleic acid turning negative and improve the lung conditions detected by CT imaging, reduce the duration of hospital stay and cough time of the patient, rapidly increase white blood cells, reduce the CRP response, indicating the reduced production of inflammatory stress proteins. The effect of the combination of the agents is much better than the conventional treatment of novel coronavirus pneumonia.

In addition, the combined treatment of TFF2 protein and IFN-κ protein can significantly increase the number of white blood cells in the blood, and has no effect on lymphocytes, platelets, and hemoglobin. It shows that it has no obvious toxicity to liver, blood cells and platelets.

In conclusion, the combination of TFF2 protein and IFN-κ protein can be effectively and safely used for the treatment of novel coronavirus infection.

Example 5. Comparison of the efficacy of the combination of TFF2 protein and IFN-κ protein with hydroxychloroquine on patients with novel coronavirus Enrolled Subjects Common patients with COVID-19.

Dosing Regimen (1) Control group: standard treatment (excluding the administration of hydroxychloroquine), designated as the NC group;
(2) Hydroxychloroquine group: on the basis of standard treatment, 100 mg of hydroxychloroquine taken orally once a day, designated as "Standard treatment+hydroxychloroquine";
(3) TFF2+IFN-κ group: on the basis of standard treatment, combined formulation (5 mg TFF2 protein+1 mg IFN-κ protein) for inhalation, designated as "Standard treatment+protein combination atomization";

(4) Comprehensive treatment group: on the basis of standard treatment, oral administration of 100 mg of hydroxychloroquine once a day, and combined formulation (5 mg of TFF2 protein+1 mg of IFN-κ protein) for aerosol inhalation, designated as "Standard treatment+hydroxychloroquine+(TFF2 protein)+IFN-κ protein)".

Trial Results and Discussion

Figure 13:
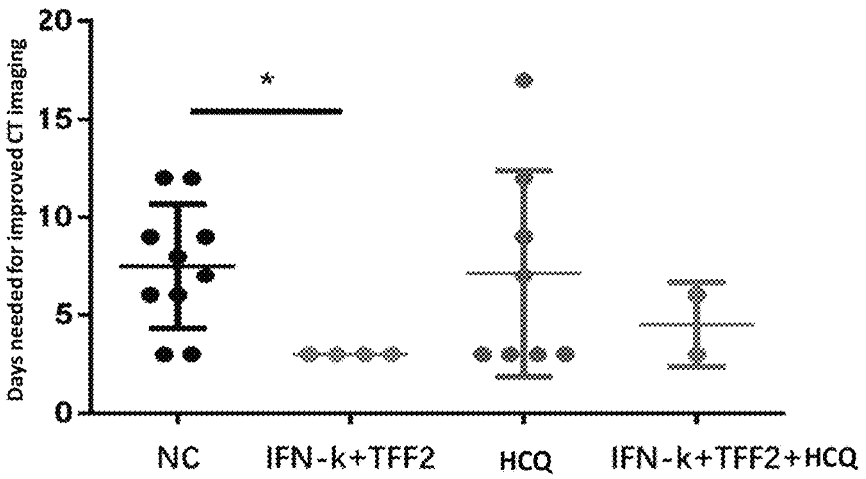
FIG. 13: The effect of the combined administration of TFF2 protein and IFN-κ protein and hydroxychloroquine (HCQ) treatment on the number of days required for CT improvement in patients with novel coronavirus.
Figure 14:
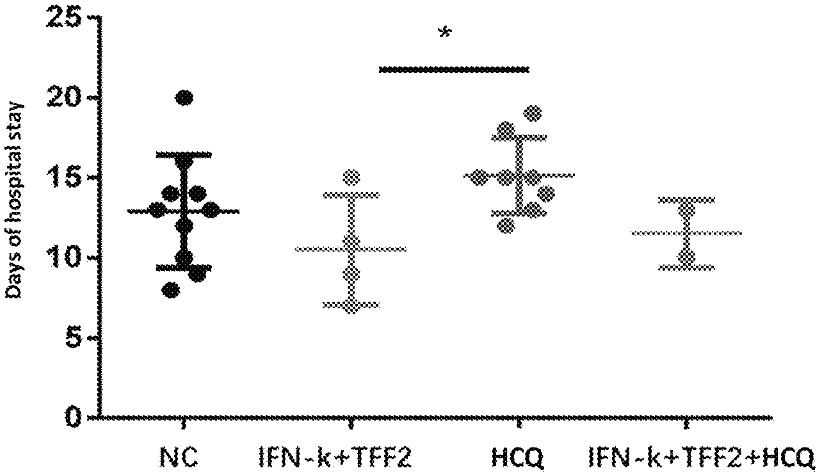
FIG. 14: The effect of the combined administration of TFF2 protein and IFN-κ protein and hydroxychloroquine treatment on the length of hospital stay in patients with novel coronavirus.
Figure 15:
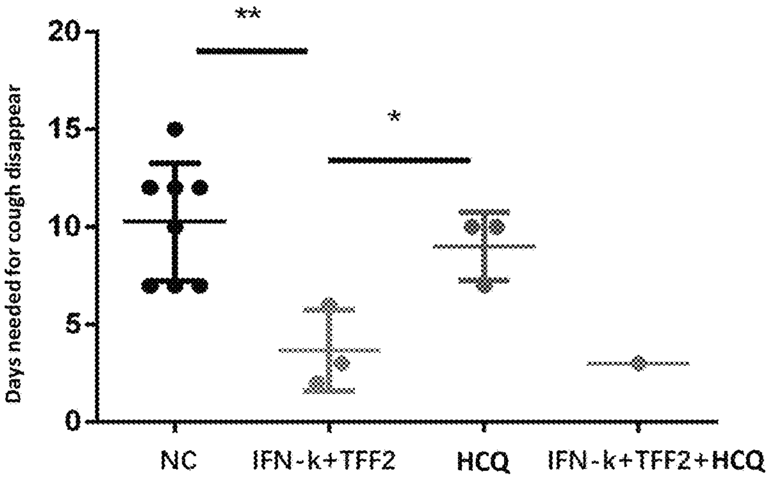
FIG. 15: The effect of the combined administration of TFF2 protein and IFN-κ protein and hydroxychloroquine treatment on the number of days required for the cough to disappear in patients with novel coronavirus.

The trial results are shown in FIGS. 13-15. The results show:

Compared with the control group, both the combination of TFF2 protein & IFN-κ protein, and hydroxychloroquine treatment can accelerate the relief and recovery of the symptoms of the novel coronavirus patients. The CT imaging improvement time, duration of hospital stay and cough elimination time of these groups were shortened. The effect of combined treatment with IFN-κ protein was more obvious.

Moreover, compared with hydroxychloroquine treatment, the combination of TFF2 protein with IFN-κ protein significantly shortened the duration of hospital stay, significantly relieved cough symptoms, and stably improved lung condition detected by CT imaging.

In addition, the further treatment of hydroxychloroquine on the basis of the combination of TFF2 protein with IFN-κ protein did not improve the therapeutic effect compared with the combination of TFF2 protein with IFN-κ protein, which further proved the therapeutic effect of the combination of TFF2 protein with IFN-κ protein.

The above results show that the combination of TFF2 protein with IFN-κ protein can be effectively used for the treatment of novel coronavirus pneumonia, and its effect is even significantly better than the clinically recommended drug hydroxychloroquine. In view of the fact that TFF2 protein and IFN-κ protein are both endogenous proteins and the safety demonstrated above, the combination of these two proteins is highly expected to be the preferred therapy for the treatment of novel coronavirus infection.

Attachment: Sequence Listing Information

| SEQ ID NO | Sequence name |
|---|---|
| 1 | Amino acid sequence of recombinant human hTFF2 protein |
| 2 | Amino acid sequence of recombinant mouse mTFF2 protein |
| 3 | Full-length sequence of hTFF2 gene |
| 4 | hTFF2 cDNA sequence |
| 5 | Full-length sequence of mTFF2 gene |
| 6 | mTFF2 cDNA sequence |
| 7 | Amino acid sequence of recombinant human hIFN-κ protein |
| 8 | Amino acid sequence of recombinant mouse mIFN-κ protein |
| 9 | Full-length sequence of hIFN-κ gene |
| 10 | hIFN-κ cDNA sequence |
| 11 | Full-length sequence of mIFN-κ gene |
| 12 | mIFN-κ cDNA sequence |
| 13 | TFF2 forward primer |
| 14 | TFF2 reverse primer |
| 15 | IFN-κ forward primer |
| 16 | IFN-κ reverse primer |

All documents mentioned in this disclosure are incorporated by reference in this application as if each document were individually incorporated by reference. In addition, it should be understood that after reading the above teaching content of the present disclosure, those skilled in the art can make various changes or modifications to the present disclosure, and these equivalent forms also fall within the scope defined by the appended claims of the present application.

What is claimed is:

1. A method for treating novel coronavirus infection in a subject in need thereof, the method comprising administering to the subject an effective amount of a product comprising (a) a TFF2 protein, wherein said TFF2 protein is selected from: a polypeptide of the sequence set forth in SEQ ID NO: 1 or 2 or a polypeptide encoded by the nucleic acid molecule set forth in any of SEQ ID NOs: 3-6;

(b) an IFN-κ protein, wherein said IFN-κ protein is selected from: a protein of the sequence set forth in SEQ ID NO: 7 or 8 or a polypeptide encoded by the nucleic acid molecule set forth in any of SEQ ID NOs: 9 to 12; and (c) optionally, a pharmaceutically acceptable carrier.

2. The method of claim 1, wherein the novel coronavirus infection has a related conditions of novel coronavirus pneumonia.

3. The method of claim 1, wherein the subject is a human.

4. The method of claim 1, wherein the product is a pharmaceutical composition, a combined formulation, or a kit.

5. The method of claim 4, wherein the amount of said TFF2 protein ranges from 0.1 to 100 mg, from 0.5 to 50 mg, from 1 to 40 mg, or from 5 to 30 mg; and/or wherein the amount of the IFN-κ protein ranges from 0.01 to 100 mg, from 0.05 to 80 mg, from 0.1 to 70 mg, or from 0.5 to 50 mg.

6. The method of claim 1, wherein the mass ratio of TFF2 protein to IFN-κ protein ranges from 1:100 to 100:1, from 1:50 to 50:1, from 1:10 to 10:1, from 1:5 to 5:1, from 1:2 to 2.5:1, or from 1:1 to 2:1.

7. The method of claim 1, wherein the administration of TFF2 protein and IFN-κ protein is by the same or different routes selected from the group consisting of: aerosol inhalation, nasal instillation, spray, intravenous administration, target tissue administration, or oral administration.

8. The method of claim 1, wherein the TFF2 protein and IFN-κ protein in the product is simultaneously, sequentially, or intervally administered.

* * * * *